United States Patent [19]
Orning et al.

[11] Patent Number: 5,837,684
[45] Date of Patent: Nov. 17, 1998

[54] PEPTIDES

[75] Inventors: Lars Orning; Beate Arbo; Peter Fischer; Kjell S. Sakariassen, all of Oslo, Norway

[73] Assignee: Nycomed Imaging AS, Oslo, Norway

[21] Appl. No.: 479,223

[22] Filed: Jun. 7, 1995

[51] Int. Cl.$^6$ .......................... A61K 38/04; C07K 16/00; C07K 17/00; C07K 5/00

[52] U.S. Cl. .............................. 514/15; 530/328; 530/384

[58] Field of Search .................................... 530/328, 384; 514/15

[56] References Cited

U.S. PATENT DOCUMENTS 5,110,730  5/1992  Edgington et al. ..................... 435/69.6

OTHER PUBLICATIONS

Y. Nemerson, *Blood,* vol. 71, No. 1, 1988, pp. 1–8.
Gailani and Broze et al, *Science* 253, pp. 909–912.
Weiss et al, vol. 73, No. 4, *Blood*, 1989, pp. 968–975.
Furie B. and Furie, B.C. The New England Journal of Medicine, vol. 326, 800, 1992.

*Primary Examiner*—Cecilia J. Tsang
*Assistant Examiner*—S. G. Marshall
*Attorney, Agent, or Firm*—Bacon & Thomas

[57] ABSTRACT

Peptide reagents and compositions thereof which reduce blood clotting initiated by the ternary complex of tissue factor (TF), FVIIa and FXa. The peptides have the amino acid sequences Thr—Leu—Tyr—Tyr—Trp—Arg—Ala—Ser—Ser—Thr (SEQ. ID. NO: 3) and Ile—Ile—Thr—Tyr—Arg—Lys—Gly—Ser—Ser—Thr (SEQ. ID. NO: 2).

6 Claims, 2 Drawing Sheets

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO: 1:

```
Thr  Leu  Tyr  Tyr  Trp  Lys  Ser  Ser  Ser  Ser
 1                    5                        10
```

( 2 ) INFORMATION FOR SEQ ID NO: 2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 2:

```
Ile  Ile  Thr  Tyr  Arg  Lys  Gly  Ser  Ser  Thr
 1                    5                        10
```

( 2 ) INFORMATION FOR SEQ ID NO: 3:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO: 3:

```
Thr  Leu  Tyr  Tyr  Trp  Arg  Ala  Ser  Ser  Thr
 1                    5                        10
```

PEPTIDES

BACKGROUND OF THE INVENTION

1. Field of the Invention

The present invention is concerned with peptide reagents and compositions thereof which reduce blood clotting initiated by the ternary complex of tissue factor (TF), FVIIa and FXa. Reducing the formation of FX coagulant activity (FXa) by interfering with the formation of the ternary complex TF/FVIIa/FXa inhibits TF-dependent blood clotting. Thus the extrinsic pathway of coagulation is inhibited.

2. Background Art

Blood clotting relies upon a cascade of enzymatic reactions which eventually results in the formation of a fibrin clot (Furie B. & Furie B. C.: Molecular and cellular biology of blood coagulation. N. Eng. J. Med. 326, 800, 1992). The triggering mechanism is either initiated by contact with an artificial surface (intrinsic coagulation pathway) or by TF at a vessel wall lesion (extrinsic coagulation pathway). The process of blood coagulation is a defense mechanism which prevents blood loss following vessel wall injury (hemostasis). However, a similar process may also be triggered at a vascular lesion where blood loss is not a threat, but which unfortunately may result in thrombus formation (thrombogenesis). It is thought that the extrinsic pathway of coagulation is the dominating one in vivo, both in hemostasis and thrombosis (Gailani D. & Broze G. J.: Factor IX activation in a revised model of blood coagulation. Science 253, 909, 1991, and Nemerson Y.: The tissue factor pathway of coagulation. Hemostasis and Thrombosis: Basic Principles and Clinical Practice, Third Edition. Eds. R. W. Colman, J. Hirsh, V. J. Marder & R. W. Salzman. J. B. Lippincott Company, Philadelphia, p81, 1994).

FX is activated by the catalytic activity of the binary TF/FVIIa complex in the presence of $CA^{2+}$ on phospholipid-rich surfaces (Nemerson Y.: Tissue Factor and Hemostasis. Blood 71, 1, 1988). During this event, FX complexes with the preformed TF/FVIIa complex and is subsequently activated and released. Thus, a ternary complex is formed which has FX coagulant activity (FXa). Activation of this extrinsic pathway of coagulation leads to fibrin formation which apparently is of prime importance in development of arterlosclerotic lesions and in reocclusion and restenosis following endarterectomy (Weiss II. J., Turitto V. T., Baumgartner H. R., Nemerson Y. & Hottmann T.: Evidence for the presence of tissue factor activity on subendothelium. Blood 73, 968, 1989; Hultin M. S.: Fibrinogen and factor VII as risk factors in vascular disease. Progress in Hemostasis and Thrombosis. Volume 10, Ed. B. S. Coller, W. B. Saunders, Philadelphia, p215, 1991; and Jang I. K., Gold H. K., Leinback R. C., Fallon J. T., Collen D. & Wilcox J. N.: Antithrombotic effect of a monoclonal antibody against tissue factor in a rabbit model of platelet-mediated arterial thrombosis. Arterioscler. Tromb. 12, 948, 1992). Relatively little is known about the molecular interactions between TF and FVIIa and between TF/FVIIa and FX.

Mouse TF, in contrast to rabbit TF, does not support the procoagulant activity of human FVIIa on FX (Andrews B. S., Rehemtulla A., Fowler B. J., Edgington T. S. & Mackman N.: Conservation of tissue factor sequence among three mammalian species. Gene 98, 265, 1991). Whether this effect is due to lack of compatibility between mouse TF and human FVII and/or FX is not known. Recently, three putative binding sites for FVIIa and one for FX were identified in human TF (Harlos K., Martin D. M. A., O'Brien, Jones E. Y., Stuart D. I., Polikarpov I., Miller A., Tuddenham E. G. O. & Boys C. W. G.: Crystal Structure of the extracellular region of human tissue factor. Nature 370, 662, 1994). When studying the species homology for these binding regions, we found striking homology for the putative FVIIa binding sites (>80% for 10 residues comprising putative FVIa binding sites). However, for the FX recognition site there is low homology between man and mouse (40% for 10 residues, residues are identified below), whereas the homology between man and rabbit is higher (70% for 10 residues, residues are identified below). It therefore seemed likely that the incompatability between man and mouse TF and human FVIIa and/or FX is localized to this region, resulting in impaired FX binding and FX activation. The putative FX binding site on the TF molecule is outlines below:

FX Putative Binding Site

Rabbit: (SEQ. ID. NO: 3) 152—Thr—Leu—Tyr—Tyr—Trp—Arg—Ala—Ser—Ser—Thr—161 (70%)

Man: (SEQ. ID. NO: 1) 154—Thr—Leu—Tyr—Tyr—Trp—Lys—Ser—Ser—Ser—Ser—163

Mouse: (SEQ. ID. NO: 2) 158—Ile—Ile—Thr—Tyr—Arg—Lys—Gly—Ser—Ser—Thr—167 (40%)

Site-directed mutagenesis of TF as well as synthetic peptides has in addition indicated a domain of the TF molecule which appears important for the activation of FX by the binary TF/FVIIa complex (Edgington T. S. & Morrissey J. H., U.S. Pat. No. 5,110,730, May 5, 1992). This domain is located at residues 152–169 of the mature TF molecule.

We have surprisingly found that peptides of smaller side (10-mers), and not based on the primary sequence of human TF, are very potent inhibitors or TF-dependent coagulation in humans.

SUMMARY OF THE INVENTION

The invention thus provides peptides having the amino acid sequences Ihr—Leu—Tyr—Tyr—Trp—Arg—Ala—Ser— Ser—Thr and Ile—Ile—Thr—Tyr—Arg—Lys—Gly—Ser—Ser—Thr, all (SEQ. ID. NO: 2) amino acids other than glycine being in the conventional L form.

The invention also provides the abovementioned peptides for use in the treatment or prevention of blood clotting disorders or problems in a human subject.

DETAILED DESCRIPTION OF THE INVENTION AND PREFERRED EMBODIMENTS

The peptides of the invention differ from those of previous publications in this particular area and from the above cited patent, since they are not based on the primary sequence of human TF. In contrast, they have primary sequences identical to murine and rabbit TF, showing 40% and 70% homology respectively with human TF. Furthermore, kinetic analysis reveals that both peptides inhibit extrinsic coagulation by competing with the binary complex of TF/FVIIa for FX. This implies that the conversion of FX to FXa by the TF/FVIIa complex is inhibited. Thus, the peptides have unique amino acid sequences, inhibitory capacity in a relevant bioassay and a well established mechanism of inhibition. Such inhibitors represent a novel approach for inhibition of coagulation and thrombus formation in humans. As such, these peptide and compositions thereof may be used as human antithrombotics, both in prophylaxis and treatment.

The activity of the peptide Ile—Ile—Thr—Thr—Arg—Lys—Gly—Ser—Ser—Thr (SEQ. ID. NO: 2) is particularly surprising given that native mouse TF does not support the human procoagulant activity of human FVIIa on FX (see the reference cited above).

Figure 1:
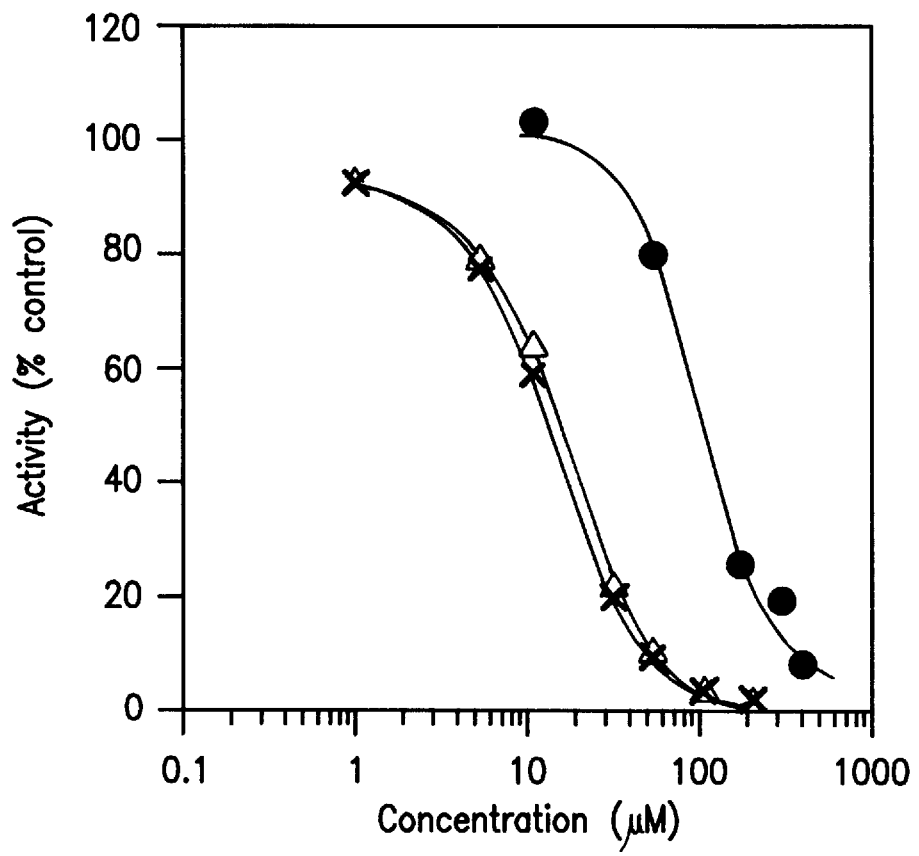
FIG. 1 is a graph which shows activity of the peptides (SEQ. ID. NO: 1), (SEQ. ID. NO: 2), and (SEQ. ID. NO: 3) on the vertical axis versus the concentration of the peptides on the horizontal axis.

The inhibitory capacity of the peptides was measured by a so-called lipidated TF assay which is a chromogenic assay measuring the FXa generated by the binary complex of TF/FVIIa. FVIIa (5 pM final concentration) and FX (20 nM) were combined in the presence of different concentrations of peptide and incubated for 15 min at ambient temperature. TF (5 pM) and $CaCl_2$ (5 mM) were added to initiate the reaction. Reactions were quenched with EDTA and the FXa activity was measured in an amidolytic assay, using the chromogenic FXa substrate S2765 (trade name). Data from these studies with this assay are shown in FIG. 1, and Table 1 hereinafter gives the corresponding IC values. Data are plotted as the percentage of the rate of FXa formation determined without peptide versus the concentration of the following peptides: hu#154–163 (SEQ. ID. NO. 1) (●), mu#158–167 (SEQ. ID. NO. 2) (x) and rb#152–161 (SEQ. ID. NO. 3) (Δ). It is noted that the IC values for mu#158–167 (SEQ. ID. NO. 2) and rb#152–161 (SEQ. ID. NO. 3) are in the very low $\mu$m range.

TABLE 1

Inhibition of FXa formation by synthetic TF peptide analogs.

| Peptide | aa sequence | IC50 ($\mu M$)[a] |
|---|---|---|
| hu#154–163 (SEQ ID NO:1) | Thr—Leu—Tyr—Tyr—Trp Lys—Ser—Ser—Ser—Ser | 100[b] |
| mu#158–167 (SEQ ID NO:2) | Ile—Ile—Thr—Tyr—Arg— Lys—Gly—Ser—Ser—Thr | 21 |
| rb#152–161 (SEQ ID NO:3) | Thr—Leu—Tyr—Tyr—Trp— Arg—Ala—Ser—Ser Thr | 14 |

[a]The concentration of peptide inhibiting the rate of FX activation by 50%.
[b]The IC50 value may be underestimated because of difficulties in dissolving the peptide.

Figure 2A:
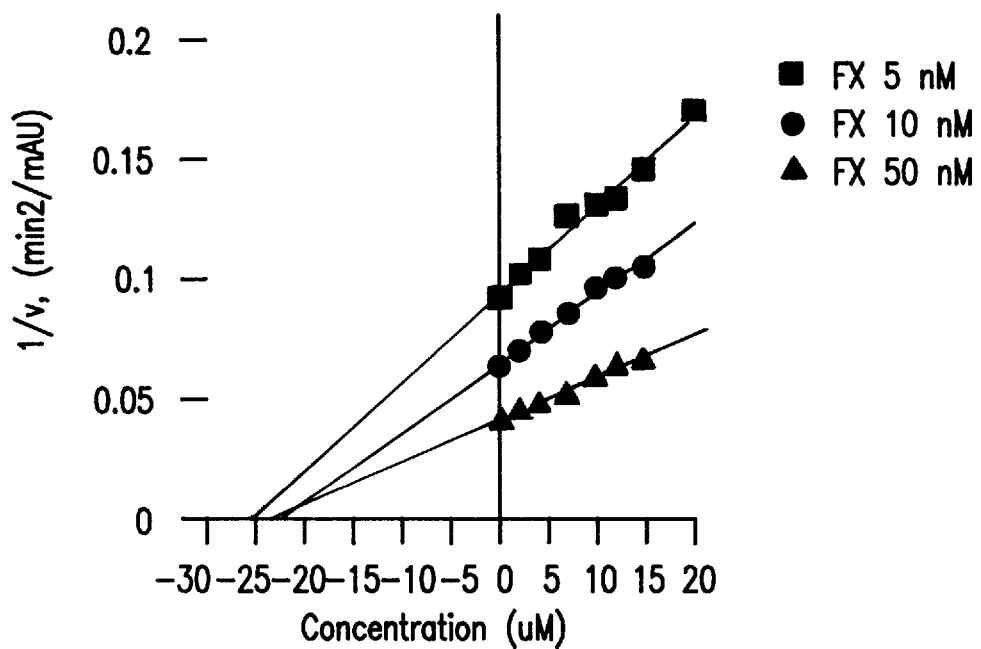
FIGS. 2a and 2b are Dixon Plot graphs which illustrate the inhibitory mechanism of FXa formation obtainable by this invention. The inverse of the rate of FXa is on the vertical axis and the peptide concentration is on the horizontal axis.
Figure 2B:
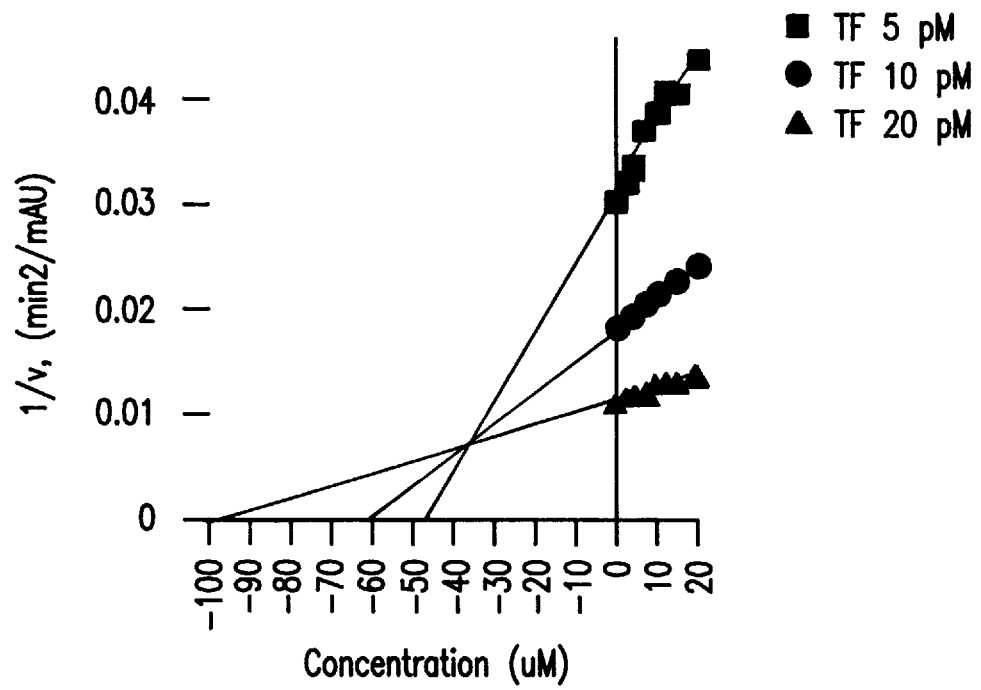

The inhibitory mechanism of FXa formation was elucidated by analysis of Dixon plots as shown in FIGS. 2A and 2B. Different concentrations of peptide were mixed with FVIIa and three different concentrations of FX and, after addition of TF, the rate of FXa formation was determined. In another experiment, different concentrations of peptide were mixed with FVIIa and three different concentrations of TF, in excess of FVIIa. After addition of FX, the rate of FXa formation was determined. Results were plotted according to Dixon, the inverse of the rate of FXa formation versus peptide concentration. Peptide mu#158–167 (SEQ. ID. No. 2), produced linear regression lines, which intercepted on the abscissa (different FX concentrations) or above the abscissa (different TF concentrations). These results are consistent with a mechanism where the peptide mu#158–167 (SEQ. ID. NO. 2) competes with TF or FVIIa/TF complex for interaction with FX.

Thus, it is possible that the mouse and rabbit peptides have conformations mimicking the FX binding site of the binary human TF/FVIIa complex in spite of the low sequence homologies.

The present invention also provides pharmaceutical compositions containing one or more of the peptides of the invention of salts thereof.

Salts of the peptides include physiologically acceptable acid addition salts such as the hydrochloride.

The compositions according to the invention may be presented, for example, in a form suitable for nasal or parenteral administration.

Thus the compounds according to the invention may be presented in the conventional pharmacological forms of administration, such as nasal sprays, solutions and emulsions. Conventional pharmaceutical excipients as well as the usual methods of production may be employed for the preparation of these forms. Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Nasal sprays may be formulated similarly in aqueous solution and packed into spray containers either with an aerosol propellant or provided with means for manual compression. Capsules containing one or several active ingredients may be produced, for example, by mixing the active ingredients with inert carriers, such as lactose or sorbitol, and filling the mixture into gelatin capsules.

Dosage units containing the compounds of this invention preferably contain 0.1–10 mg, for example 1–5 mg of the peptide or salt thereof.

As indicated above, one aspect of the invention provides peptides according to the invention for use in the treatment or prevention of blood clotting disorders or problems in a human subject. Blood clotting disorders include thrombosis (particularly vascular thrombosis or deep vein thrombosis), acute myocardial infarction, restenosis, reclosure, angina, cerebrovascular disease, peripheral arterial occlusive disease, hypercoagulability and pulmonary embolism. The peptides according to the invention can also be used to prevent occurrence of blood clotting problems caused by, for example, injury to blood vessels during thrombolytic therapy, grafting surgery, vessel patency restoration etc. Blood clotting disorders may be triggered by sepsis due to production of TNF-α or IL-1.

In a still further aspect, the present invention also provides a method of treatment of blood clotting disorders in the human body, said method comprising administering to said body one or more peptides according to the invention or salts thereof. Prophylactic methods of treatment are also provided, whereby a peptide according to the invention is administered to a patient to prevent or reduce the occurrence of possible blood clotting problems, for example during surgery or other invasive techniques. The peptide will of course normally be administered in the form of a pharmaceutically acceptable composition.

In another aspect, the present invention provides a process for the preparation of the peptides according to the invention.

The peptides of the present invention can be prepared by methods known in the art. Typically, the desired sequences are assembled by solid-phase peptide synthesis. Standard procedures for the synthesis strategy employed for the examples of this invention are described in E. Atherton & R. C. Sheppard, Solid phase peptide synthesis: a practical approach, 1989, IRL Press, Oxford. For example, a synthesis resin with an acid-labile linker group, to which the desired protected C-terminal amino acid residue has been esterified, is used. In the following example, so-called TentaGel resins with a trityl-derived linker were applied (Bayer, E., Clausen, N., Goldammer, C., Henkel, B., Rapp, W. & Zhang, L. (1994) in *Peptides: Chemistry, Structure and Biology* (Hodges, R. S. & Smith, J. A., eds.), pp. 156–158, ESCOM Leiden). The amino-protecting group is then removed and the second amino acid in the sequence is coupled using a suitable condensation reagent. Amino acids with semipermanent amino protecting groups and permanent protecting groups for the functional side chains are employed. Amino-deprotection and coupling cycles are then repeated in alternating steps until the sequence of interest is assembled. Finally the permanent side-chain protecting groups are removed and the peptide is cleaved from the synthesis resin, usually simultaneously through treatment with a suitable acidic reagent.

Alternatively, the peptides can by synthesised through solution peptide synthesis methods known in the art, either in a step-wise manner from the carboxyl terminus and/or through the application of segment condensation or ligation methods, employing comprehensive or minimal protection strategies. Combined solution-solid phase segment condensation approaches can also be applied.

Generally, the reactive groups present (for example amino, hydroxyl, thiol and carboxyl groups) will be protected during overall synthesis as indicated above. The final step in the synthesis will thus be the deprotection of a protected derivative of the peptides of the invention. A wide choice of protecting groups for amino acids is known (see, e.g., Greene, T. W. & Wuts, P. G. M. (1991) *Protective groups in organic synthesis,* John Wiley & Sons, New York). Thus for example amino protecting groups which may be employed include 9-fluoroenylmethoxycarbonyl (Fmoc), benzyloxycarbonyl, t-butyloxycarbonyl, etc. It will be appreciated that when the peptide is build up from the C terminal end, an amino-protecting group will be present on the α-amino group of each new residue added and will need to be removed selectively prior to the next coupling step. One particularly useful group for such temporary amine protection is the Fmoc group which can be removed selectively by treatment with piperidine in an organic solvent. Carboxyl protecting groups which may for example be employed include readily cleaved ester groups such as t-butyl and benzyl, as well as esters with solid phase-bound linkers, e.g. p-alkoxybenzyl, trityl, etc. It will be appreciated that a wide range of other such groups are known in the art. The use of all such protecting groups and the processes described above falls within the scope of the present invention.

The invention is illustrated by the following Examples.

EXAMPLE 1
H—Thr—Leu—Tyr—Tyr—Trp—Lys—Ser—Ser—Ser—Ser—OH (huTF residues 154–163) (SEQ. ID. NO: 1)

The peptidyl resin corresponding to the above sequence was assembled on Fmoc—Ser(Bu$^t$)—[TentaGel S Trt resin] (0.2 mmol/g; from Rapp Polymere GmbH, Túbingen, Germany) using an Applied Biosystems model 433A peptide synthesizer. Fmoc deprotection was achieved with conductivity monitoring using 20% piperidine in N-methylpyrrolidone (NMP). The washing solvent was NMP. The residues (from the carboxyl terminus) were assembled using double couplings with 10-fold molar excess of Pmoc-amino acids and 2-(1H-benzotriazol-1-yl)-1,1,3,3-tetramethyluronium-hexafluorophosphate (HBTU)/1-hydroxybenzotriazole (HOBt)/Pr$^i{}_2$NEt in NMP using 75 min coupling cycles. Prior to Fmoc-deprotection at each sequence position capping was carried out using a solution of acetic anhydride (4.7% v/v)/Pr$^i{}_2$NEt (2.2% v/v)/HOBt (0.2% w/v) in N,N-dimethylformamide. The amino acid-side chain protecting groups used were t-butoxycarbonyl for Lys and t-butyl for Ser, Thr and Tyr. The final Fmoc-deprotected and washed (dichloromethane) peptidyl resin was dried in vacuo. An aliquot (300 mg) was treated with a mixture containing phenol, 1,2-ethanedithiol, thioanisole, water and CF$_3$COOH 0.75:0.25:0.5:0.5:10, w/v/v/v/v) for 3 h. The resin residue was then filtered off and washed with small quantities of neat CF$_3$COOH. The combined filtrate and washings were triturated with Et$_2$O to obtain the crude peptide. The precipitate was collected by filtration, washed with Et$_2$O and then taken up in 0.1% aq CF$_3$COOH and lyophilised. An aliquot (25 mg) of the crude product was redissolved in 0.1% aq CF$_3$COOH (3 mL), filtered and purified by preparative RP-HPLC. The column (Vydac 218TP1022, 2.2×25 cm) was eluted at 10 ml/min with a gradient of 0 to 20% MeCN in 0.1% aq CF$_3$COOH over 90 min. Appropriate peak fractions were pooled and lyophilised to afford 12 mg of pure peptide. Analytical RP HPLC: $t_R$–19.6 min, purity 99% (Vydac 218TP54, 0.46×25 cm, 0–30% MeCN in 0.1% aq CF$_3$COOH over 20 min at 1 ml/min, λ=215 nm). FAB MS: [M+II]$^+$=1221.6 m/z, C$_{57}$H$_{81}$N$_{12}$O$_{18}$=1221.3. Amino acid analysis: Leu 1.01(1), Lys 1.05(1), Ser 3.96(4), Thr 1.00(1), Tyr 1.98(2), Trp was not determined.

EXAMPLE 2
H—Ile—Ile—Thr—Tyr—Arg—Lys—Gly—Ser—Ser—Thr—OH (muTF residues 158–167) (SEQ. ID. NO: 2)

The peptidyl resin corresponding to the above sequence was assembled on Fmoc-Thr(Bu$^t$)-[TentaGel R Trt resin] (0.17 mmol/g; from Rapp Polymere GmbH, Túbingen, Germany) in a similar fashion to the corresponding peptidyl resin in Example 1. The side chain protecting group used for Arg was 2,2,5,7,8-pentamethylchroman-6-sulphonyl. The completed peptidyl resin was worked up and an aliquot (500 mg) treated with the same acidolysis reagent as in Example 1. After precipitation from Et$_2$O, the product was dissolved in glacial AcOH and lyophilised. The crude product (99 mg) was redissolved in 10% aq MeCN containing 0.1% CF$_3$COOH (6 mL), filtered and purified in two batches by preparative RP-HPLC using the same conditions as described in Example 1. Appropriate peak fractions were pooled and lyophilised to afford 74 mg of pure peptide. Analytical RP-HPLC: $t_R$=14.7 min, purity 98% (Vydac 218TP54, 0.46×25 cm, 0–30% MeCN in 0.1% aq CF$_3$COOH over 20 min at 1 ml/min, λ=215 nm). FAB-MS [M+H]$^+$=1125.5 m/z, C$_{49}$H$_{84}$N$_{14}$O$_{16}$ 1125.3. Amino acid analysis: Arg 1.02(1), Gly 1.02(1), Ile 1.22(2), Lys 1.00(1), Ser 2.01(2), Thr1.95(2), Tyr 1.01(1).

EXAMPLE 3
H—Thr—Leu—Tyr—Tyr—Trp—Arg—Ala—Ser—Ser—Thr—OH (rbTF residues 152 161) (SEQ. ID. NO: 3)

The peptidyl resin corresponding to the above sequence was assembled on Fmoc—Thr(Bu$^t$)-[TentaGel R Trt resin] (0.17 mmol/g; from Rapp Polymere GmbH, Túbinge, Germany) in a similar fashion to the corresponding peptidyl resin of Example 1. The side chain protecting group used for Arg was 2,2,5,7,8-pentamethylchroman-6-sulphonyl. The completed peptidyl resin was worked up and an aliquot (520 mg dry weight) treated with the same acidolysis reagent as in Example 1. After precipitation from Et$_2$O, the product was dissolved in glacial AcOH and lyophilised. An aliquot of the crude product (40 mg) was redissolved in 10% aq MeCN containing 0.1% CF$_3$COOH (4 mL), filtered and purified by preparative RP-HPLC using the same conditions as described in Example 1. Appropriate peak fractions were pooled and lyophilised to afford 25 mg of pure peptide. Analytical RP-HPLC: $t_R$=20.6 min, purity 97% (Vydac 218TP54, 0.46×25 cm, 0–30% MeCN in 0.1% aq CF$_3$COOH over 20 min at 1 ml/min, λ=215 nm). FAB MS: [M+H]$^+$=1247.7 m/z, C$_{49}$H$_{54}$N$_{14}$O$_{16}$-1247.4. Amino acid analysis: Ala 1.01(1), Arg 1.02(1), Leu 1.00(1), Ser 1.99(2), Thr 1.97(2), Tyr 2.00(2), Trp was not determined.

We claim:

1. The peptides having the amino acid sequences Thr—Leu—Tyr—Tyr—Trp—Arg—Ala—Ser—Ser—Thr (SEQ. ID. NO: 3) and Ile—Ile—Thr—Tyr—Arg—Lys—Gly—Ser—Ser—Thr (SEQ. ID. NO: 2).

2. The peptide of claim 1 which is Ile—Ile—Thr—Tyr—Arg—Lys—Gly—Ser—Ser—Thr (SEQ. ID. NO: 2).

3. A peptide according to claim 1 wherein said peptide is prepared by solid-phase or solution synthesis.

4. A pharmaceutical composition containing a peptide according to claim 1 or a salt thereof in combination with a pharmaceutically acceptable carrier.

5. A method of treatment or prevention of a blood clotting disorder in a human body, said method comprising administering to said body a peptide according to claim 1 or a salt thereof.

6. A method of inhibiting binding or tissue factor-Factor VIIa complex to Factor X in a human subject, said method comprising administering to said subject a peptide according to claim 1 or a salt thereof.

* * * * *